(12) United States Patent
Davies et al.

(10) Patent No.: US 7,871,603 B2
(45) Date of Patent: Jan. 18, 2011

(54) INTERFERON-BETA AND/OR LAMBDA FOR USE IN TREATING RHINOVIRUS INFECTION IN THE ELDERLY

(75) Inventors: Donna Davies, Salisbury (GB); Sarah Margaret Puddicombe, Southampton (GB); Soo-Wei Foo, Concord (AU)

(73) Assignee: Synairgen Research Limited, Southampton (GB)

(*) Notice: Subject to any disclaimer, the term of this patent is extended or adjusted under 35 U.S.C. 154(b) by 154 days.

(21) Appl. No.: 12/122,510

(22) Filed: May 16, 2008

(65) Prior Publication Data

US 2009/0004139 A1  Jan. 1, 2009

Related U.S. Application Data

(60) Provisional application No. 60/938,987, filed on May 18, 2007.

(51) Int. Cl.
*A61K 38/21* (2006.01)
*A61K 48/00* (2006.01)

(52) U.S. Cl. ............... 424/85.5; 424/85.6; 514/44 R
(58) Field of Classification Search ................ None
See application file for complete search history.

(56) References Cited

FOREIGN PATENT DOCUMENTS

| WO | WO-2005/087253 | | 9/2005 |
|---|---|---|---|
| WO | WO 2005/105136 | * | 10/2005 |
| WO | WO-2007/029041 | | 3/2007 |

OTHER PUBLICATIONS

Halme et al (Respiration 61:105-107, 1994).*
Halme et al (International Journal of Radiation Oncology Biology Physics 31:930101, 1995).*
Cohen et al (American Journal of Public Health 83:1277-11283, 1993).*
Gauvreau et al (American Journal of Respiratory and Cricical Care Medicine 174:15-20, 2006).*
Rudolph et al (Molecular Therapy 12:493-501, 2005).*
McLachlan et al (Molecular Therapy 15:348-354, 2007).*
Ank et al., J Virol (2006) 80:4501-4509.
Bensenor et al., AEP (2001) 11:225-231.
Bucchieri et al., "Bronchial Epithelial Cells from Smokers Have a Poor Innate Response to Infection with Rhinovirus," presentation dated May 24, 2006, publication p. A842 [Poster Board #618].
Carrat et al., Intensive Care Med (2006) 32:156-159.
Cohen et al., Am J Public Health (1993) 83:1277-1283.
Contoli et al., Nat Med (2006) 12:1023-1026.
El-Sahly et al., Clin Infect Dis (2000) 31:96-100.
Falsey et al., J Infect Dis (2002) 185:1338-1341.
Foo et al., "In Vitro Model of Rhinoviral Infection of Primary Bronchial Epithelial Cells from Smokers," presentation dated May 24, 2006, publication p. A842 [Poster Board #616].
Higgins et al., J Interferon Res (1986) 6:153-159.
Louie et al., Clin Infect Dis (2005) 41:262-265.
Monto et al., J Infect Disease (1987) 156:43.
Pistelli et al., Eur Respir J (2003) 21:10S-14S.
Sperber et al., J Infect Dis (1989) 160:700-705.
Uze and Monneron, Biochimie (2007) 89(6-7):729-734.
Venarske et al., J Infect Dis (2006) 193:1536-1543.
Wark et al., J Exp Med (2005) 201:937-947.

* cited by examiner

*Primary Examiner*—Mary E Mosher
(74) *Attorney, Agent, or Firm*—Morrison & Foerster LLP

(57) ABSTRACT

Use of interferon-beta (IFN-β) and/or IFN-λ for treating rhinovirus (RV) infection in elderly people, particularly elderly people who are, or have been long-term smokers, especially those who have a clinical history of recurrent RV infections, and may have other medical conditions, such as cardiac or circulation problems, and who are liable to suffer severe complications/high mortality from poor innate ability to fight such a viral infection.

7 Claims, 5 Drawing Sheets

INTERFERON-BETA AND/OR LAMBDA FOR USE IN TREATING RHINOVIRUS INFECTION IN THE ELDERLY

CROSS-REFERENCE TO RELATED APPLICATIONS

This application claims priority from U.S. provisional application No. 60/938,987 filed May 18, 2007. The contents of this document are incorporated by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 255352002900Seqlist.txt | Jun. 30, 2008 | 2,437 bytes |

TECHNICAL FIELD

The present invention relates to new use of interferon-beta (IFN-β) and/or IFN-λ in relation to treating rhinovirus (RV) infection in elderly people, particularly elderly people who are, or have been long-term smokers, and/or are suffering from conditions other than asthma and COPD, e.g. cardiac or circulation problems (Carrat et al. (2006) Intensive Care Med. 32, 156-159). While in otherwise healthy young people, rhinovirus infection, the main cause of the common cold, tends to be merely a nuisance which is generally fought off by the body's immune system, RV infection is well-known to have increased liability to cause medical complications in the elderly, especially those with a history of smoking and/or those who have other medical problems (Cohen et al. (1993) Am. J. Public Health 83, 1277-1283; Pistelli et al. (2003). Eur. Respir. J. 21:10S-14S; El-Sahly et al. (2000) Clin. Infect. Dis. 31, 96-100). The invention is envisaged as particularly useful in relation to such elderly individuals who have a clinical history of recurrent RV problems.

BACKGROUND ART

Data published by researchers at the University of Chicago (Monto et al. (1987) J. Infect. Disease 156, 43 (see Table 2 in the exemplification), has previously shown that RV infection complications increase with age, with lower respiratory tract problems increasing considerably in the 40 or over age group reflected by increased physician consultation. Other studies have also indicated that elderly people, e.g. in care, are more susceptible to severe illness and mortality through RV infection than younger population groups (Louie et al. (2005) Clin. Infect. Dis. 41, 262-265; Falsey et al. (2002) J. Infect. Dis. 185, 1338-1341). This is consistent with decline in innate immunity in the elderly, and with poorer responses to flu vaccinations. Smokers have also been shown to be more susceptible to respiratory tract infections and to the prolonged effects of virus infections such as RV infections (Cohen et al. (1993) ibid; Benseñor et al. (2001) AEP 11, 225-231; Venarske et al. (2006) J. Infect Dis. 193, 1536-1543). Individuals with chronic underlying illnesses such as congestive heart failure are also highly susceptible to the effects of RV infections (El-Sahly et al. (2000) Clin Infect Dis. 31, 96-100).

While IFN-β has previously been known to have anti-viral activity, including in relation to RV infection in in vitro cellular studies and in clinical trials with purposely RV-infected individuals, up to now it has only been proposed, however, for clinical use in relation to RV infection in the context of RV-exacerbation of asthma and chronic obstructive pulmonary disease (COPD). In asthmatics and COPD sufferers, it has been found that there is deficiency of IFN-β production in bronchial epithelial cells in response to RV infection and airway delivery of IFN-β in such patients is thus indicated to prevent or treat RV infection which may otherwise cause severe exacerbation of asthma or COPD (see published International Application WO 2005/087253 and Wark et al. (2005) "Asthmatic bronchial epithelial cells have a deficient innate immune response to infection with rhinovirus" J. Exp. Med. 201, 937-947).

IFN-λ production has also been shown to be deficient in bronchial epithelial cells of asthmatics when challenged with RV infection (published International Application WO 2007/029041). Expression of type I IFN-α/βs and type III IFN-λs are induced in response to known inducers (e.g. viral RNA/DNA, LPS) suggesting overlapping signalling mechanisms leading to their expression (Ank et al. (2006) "Lambda interferon (IFN-lambda), a type III IFN, is induced by viruses and by IFNs such as IFNβ and displays potent antiviral activity against select virus infections in vivo" J. Virol. 80, 4501 and Uzé et al. (2007) "IL-28 and IL-29: Newcomers to the IFN family" Biochimie epub ahead of print xx, 1-6). Although IFN-λs bind to a different receptor than that for Type I interferons, the interferon responsive genes and the antiviral response triggered by these two classes of interferons appear to be equivalent (Ank et al (2006) ibid). Hence, IFN-λ has also been proposed for treating viral exacerbation of asthma and COPD, especially, for example, such exacerbation by RV and influenza infection (see published International Application WO 2007/029041 and Contoli et al. (2006) "Role of deficient type III interferon-λ production in asthma exacerbations" Nat Med. 12, 1023-1026).

In contrast, use of IFN-β in individuals with RV infection but who are otherwise healthy has been thought to have no true experimental support. Although the first clinical trial using IFNβ-ser against experimental rhinovirus infection showed promising beneficial results (Higgins et al. (1986) "Interferon-beta ser as prophylaxis against experimental rhinovirus infection in volunteers" J. Interferon Res. 6, 153-159), in a subsequent trial for prophylaxis of natural colds by intranasal delivery, IFNβ-ser was found to be ineffective (Sperber et al. (1989) "Ineffectiveness of recombinant interferon-beta serine nasal drops for prophylaxis of natural colds" J. Infect. Dis. 160, 700-705). This may be accounted for by the innate capacity of RV-infected cells to produce IFN-β in response to such infection.

Evidence is now presented indicating however that such innate capacity is compromised in elderly people, especially long-term smokers. Unexpectedly, and more particularly, cultured bronchial epithelial cells from such smokers have been found to exhibit increased RV-induced cytotoxicity and IFN-β has been shown to protect against such cytotoxic cell death. Hence, clinical utility for airway delivery of IFN-β in elderly people with RV infection, whether or not smokers, whether or not asthmatic or suffering from COPD, is now indicated. Such utility is also extrapolated to IFN-λ.

SUMMARY OF THE INVENTION

In one aspect of the invention, there is thus provided use of one or more agents selected from:
(i) IFN-β and/or IFN-λ;
(ii) agents that increase IFN-β and/or IFN-λ expression and
(iii) polynucleotides which express one or more agents as in (i) or (ii) in human bronchial epithelial cells in the manufacture of a medicament for airway delivery to treat or protect against RV-infection in non-asthmatic/non-COPD human individuals of age 40 plus, more preferably age 50 to 55 plus, more especially age 60 to 65 plus, e.g. 65 to 70 plus or 75 plus, preferably such individuals who are, or have been smokers such that bronchial epithelial cells (BECs) derived from such individuals exhibit increased cytotoxicity in response to RV infection compared with identically cultured BECS from non-smoker age-matched controls, e.g. when cultured with RV-16 at a multiplicity of infection (MOI) of 2 for 8 to 48 hrs (see exemplification). Such use is of especial interest where such individuals have other medical conditions and RV infection is liable to lead to complications, with the proviso that as indicated above IFN-β and IFN-λ are already recognised to be useful in the treatment of, or protection from, RV-induced exacerbation of asthma and COPD. As also noted above such use is envisaged as particularly favoured in relation to such individuals who have a clinical history of recurrent RV problems. By "protection from" will be understood any prophylactic treatment which will prevent, or at least ameliorate, the RV infection. The individuals for treatment whether smokers or non-smokers will preferably be individuals as noted above whose bronchial epithelial cells are more susceptible to RV infection compared to such cells from young healthy individuals of less than age 40.

The invention also provides one or more agents selected from:
(i) IFN-β and/or IFN-λ;
(ii) agents that increase IFN-β and/or IFN-λ expression and
(iii) polynucleotides which express one or more agents as in (i) or (ii) in human bronchial epithelial cells for airway delivery to treat individuals as noted above.

Additionally provided is a method of treating or protecting against RV-infection in a non-asthmatic/non-COPD human individual as indicated above, which comprises airway delivery of one or more agents selected from the group consisting of:
(i) IFN-β and/or IFN-λ;
(ii) agents that increase IFN-β and/or IFN-λ expression and
(iii) polynucleotides which express one or more agents as in (i) or (ii) in human bronchial epithelial cells Use of IFN-β is particularly favoured.

DETAILED DESCRIPTION

Use of IFN-β and/or IFN-λ

IFN-β for use in accordance with the invention will be understood to refer to any form or analogue or synthetic non-natural derivative of IFN-β that retains the required biological activity of native IFN-β. It may preferably be a recombinant IFN-β, e.g. a commercially available IFN-β including but not limited to recombinant IFN-β 1a, IFN-β 1b, Betaseron®, Betaferon®, Avonex®, Rebif® and formulations manufactured by Rentschler GmbH or any other manufacturer.

Similarly IFN-λ, for use in accordance with the invention may be any form or analogue or synthetic non-natural derivative of IFN-λ that retains the required biological activity of a native form, preferably a recombinant IFN-λ. Three different forms of IFN-λ are known and one or more polypeptides selected from recombinant versions or analogues of these may be employed as detailed in WO 2007/029041.

Agents that Increase IFN-β and/or IFN-λ Expression

As indicated above, the invention may also involve using an agent that increases endogenous expression of IFN-β and/or IFN-λ in bronchial epithelial cells of individuals of interest. Such agents may, for example, act directly at the gene level to increase gene expression, at the promoter or another regulatory gene sequence. Agents known to increase endogenous IFN-β expression include poly(inosinic acid)-poly (cytidylic acid) (polyIC) and the ACE inhibitors, such as perindopril.

Polynucleotides

The invention may also involve using one or more polynucleotides which express IFN-β and/or IFN-λ or an agent which increases IFN-β and/or IFN-λ in bronchial epithelial cells. The polynucleotide may, for example, encode IFN-β including variants, fragments, and chimeric proteins thereof. The polynucleotide may incorporate synthetic or modified nucleotides. Such a polynucleotide may be in the form of a vector capable of directing expression of one or more polypeptides as desired in bronchial epithelial cells. Expression vectors for this purpose may be any type of vector conventionally employed for gene therapy. They may be plasmid expression vectors administered as naked DNA or complexed with one or more cationic amphiphiles, e.g. one or more cationic lipids, e.g. in the form of DNA/liposomes. A viral vector may alternatively be employed. Vectors for expression of therapeutic proteins in the airways of human lung have previously been described, e.g. WO 01/91800 (Isis innovation); Chow et al. (1997) Proc. Nat. Acad. Sci. USA 94, 14695-14700.

Therapy

The selected agent for use in accordance with the invention will be formulated in a composition suitable for airway delivery, e.g. by means of an aerosol nebuliser. A suitable composition for airway delivery of IFN-β may, for example, be formulated as described in U.S. Pat. No. 6,030,609 by dissolving lyophilised IFN-β in a pharmaceutically acceptable vehicle such as sterile distilled water or sterile physiological saline, optionally with addition of one or more carriers, stabilizers, surfactants or other agents in order to enhance effectiveness of the IFN-β agent. One or more IFN-λ s may be similarly formulated for airway delivery. Alternatively, a dry powder formulation may be employed. Formulation/device combinations suitable for delivery to the airways include, but are not limited to, pH neutral formulations delivered by breath actuated devices and metered dose inhalers or other aerosol delivery systems.

BRIEF DESCRIPTION OF THE DRAWINGS

The following exemplification is provided to illustrate the invention; with reference to the following figures:

FIG. 2: Effects of exogenous IFN-β on cellular responses to RV-16 infection.

EXAMPLE 1

Test Recombinant IFN-β

Figure 1:
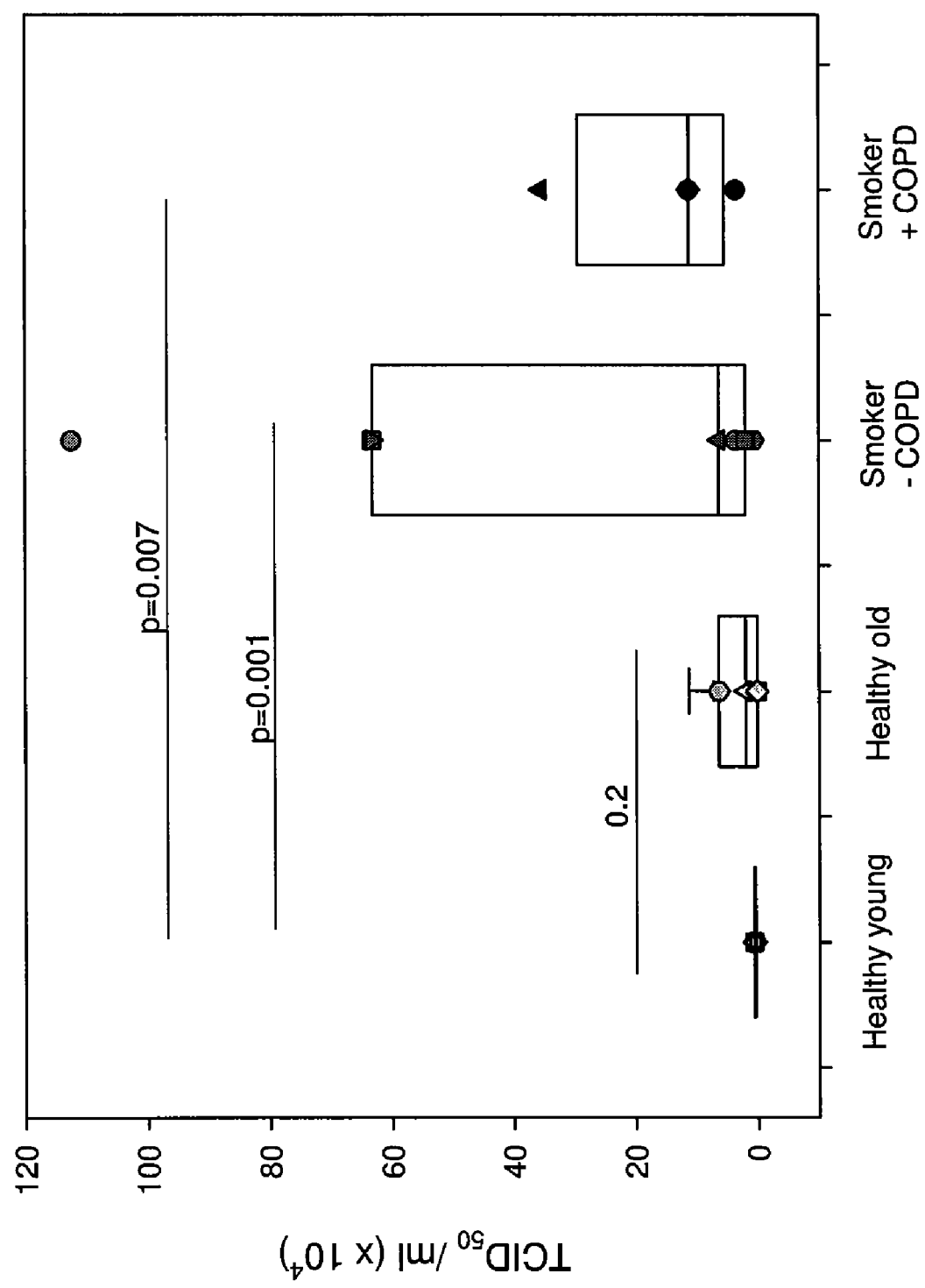
FIG. 1: Comparison of RV-16 infectious viral titre released from primary bronchial epithelial cells in relation to age and smoking status. Cells were infected with an MOI 2 and RV-16 release into the supernatant of infected cells 48 h post RV infection was determined by calculating the $TCID_{50}$/ml ($\times 10^4$) by titration assay in Ohio HeLa cells. The supernatant from non-smoking young normals (n=10), non-smoking old normals (n=9), smokers without (n=7) and smokers with COPD (n=4) were examined on titration plates. By 48 hours there was a significant increase in release of infectious RV particles in the supernatant from smokers with and without COPD compared with healthy young non-smoker control cells (p<0.001 and p=0.007 respectively). Data points represent the $TCID_{50}$/ml ($\times 10^4$). P<0.05 was considered significant.

Recombinant CHO cell derived IFN-β 1a was used from Sigma-Aldrich (product no. I 4151).

Subjects

Healthy controls had no previous history of lung disease, normal lung function, no evidence of bronchial hyper-responsiveness, and were non-atopic. The healthy controls included 10 non-smoking young controls (data published in Wark et al. (2005) ibid) and 11 non-smoking older controls. Older age-matched smokers, with and without COPD, were also included in the study as detailed in Table 1 below.

Subject Characteristics

| | Young healthy non-smoking controls | Smokers with COPD | Smokers without COPD | Age-matched older healthy non-smokers |
|---|---|---|---|---|
| Number | 10 | 9 | 9 | 11 |
| Sex (percent male) | 60% | 67% | 78% | 46% |
| Mean age (range) | 29 (24-38) | 58 (50-68) | 51 (44-64) | 56 (49-65) |
| Mean FEV 1% predicted (SD) | 110.3 (13.6) | 73.8 (12.5) | 108.6 (16.6) | 104.6 (12.9) |
| FEV/FVC | — | 61.6 (5.7) | 90.3 (21.3) | 79.1 (8.1) |

FEV 1% predicted refers to the forced expiratory volume in 1 s expressed as a percentage of the predicted value.

The study was approved by the Southampton University Hospital Ethics Committee. All subjects gave written informed consent. Subjects had no exacerbations or respiratory tract infections in the preceding 6 weeks. A detailed clinical history was recorded and a physical examination was performed. Past smoking history was measured in pack years and current smoking history was expressed as the number of cigarettes currently being smoked per day. Allergy skin tests used a panel of common aeroallergens and were considered positive if the wheal response was >3 mm than the negative control. Quality of life was assessed using the St George's Respiratory Disease Questionnaire (SGRQ); Jones et al., (1992) "A self-complete measure of health status for chronic airflow limitation." Am. Rev. Respir. Dis. 145, 1321-1327. Lung function testing consisted of spirometry (Forced Expiratory Volume in 1 second ($FEV_1$), Full Vital Capacity (FVC) and Peak Expiratory Flow Rate (PEFR)) carried out according to ATS guidelines, measurement of the residual volume to total lung capacity ratio and carbon monoxide gas transfer factor (TLCO). Bronchodilator responsiveness was measured, salbutamol (2.5 mg) was delivered via a nebuliser and post bronchodilator spirometry values were recorded. Methacholine bronchial provocation challenge was carried out as reported previously (Louis et al. (1999) Eur. Respir. J. 13, 660-667). Alpha-1 antitrypsin deficiency (COPD subjects only) status and chest X-rays were routinely performed on subjects in the healthy smoker and COPD categories. Sputum was collected to exclude infection prior to bronchoscopy. COPD was diagnosed and characterised according to the Global Initiative for Obstructive Lung Disease guidelines (GOLD) (Celli and MacNee (2004) Eur. Respir J. 23, 932-946; Fabbri and Hurd (2003) Eur. Respir. J. 22, 1-2).

Bronchial Epithelial Cell Culture

Primary bronchial epithelial cells (BECs) were grown from bronchial brushings (>95% epithelial cells), which were obtained by fibre-optic bronchoscopy in accordance with standard guidelines (Hurd, S. Z. (2006) "Workshop summary and guidelines; investigative use of bronchoscopy" J. Allergy Clin. Immunol. 88, 808-814); there was no significant difference in the proportion of columnar and basal cells isolated from non smoker, smoker without or with COPD. Cell culture and characterization was performed as described previously (Bucchieri et al. (2002) Am. J. Respir. Cell. Mol. Biol. 27, 179-185; Lordan et al. (2002) J. Immunol. 169, 407-414). The cultured cells were all cytokeratin positive and exhibited a basal cell phenotype, as evidenced by the expression of cytokeratin 13, irrespective of the type of donor of the original brushings. Primary cultures were established by seeding freshly brushed BECs into hormonally supplemented bronchial epithelial growth medium (Lonza, UK) containing 50 U/mL penicillin and 50 µg/ml streptomycin. At passage two, cells were seeded onto 12-well trays and cultured until 90% confluent, before exposure to RV-16; where indicated human IFN-β (100 IU/ml; Sigma-Aldrich) was added for 1 h prior to RV-16 infection and in cell culture media after the RV-16 exposure.

Generation and Titre of RV

RV-16 stocks were generated and titrated using infected cultures of Ohio HeLa cells as described previously (Papi and Johnson (1999) J. Biol. Chem. 274, 9707-9720). A dose response to RV infection was performed to determine the lowest multiplicity of infection (MOI) which resulted in cytopathic effects ranging from MOI 0.01-4. On this basis an MOI of 0.1 was selected for most experiments; for some experiments it was necessary to use an MOI of 2 to allow for comparison with infection of BECs from younger donors. Confirmation of infection and quantification of viral production was assessed by HeLa titration assay (Papi ad Johnson, ibid) and reverse transcription quantitative polymerase chain reaction (RT-qPCR), as described below. For negative controls, cells were treated with medium alone and UV inactivated RV-16.

Assessment of Cell Viability

Cell cytotoxicity or lysis was measured as LDH release into the culture supernatant using conversion of a sodium tetrazolium salt into a red formazan dye (Cytotox 96; Promega). The total percentage of LDH release from untreated control wells was determined at each time point analysed and cell lysis data were represented as % total cytotoxicity (LDH) or fold induction of LDH above control media.

RT-qPCR and Elisa

RT-qPCR analysis of IFN-β mRNA and RV-16 viral RNA (vRNA) gene expression was performed on DNase treated RNA extracted from BECs using TRIzol (Life Technologies). Total RNA (1 µg) was reverse transcribed using Moloney murine leukemia virus (MMLV) reverse transcriptase (Promega, Southampton, UK) with a combination of random hexamers and oligo(dT)15 for IFN-β mRNA, RV-16 vRNA, GAPDH and UBC housekeeping gene analysis. Real-time detection was performed using an iCyclerIQ detection system. The PCR cycling conditions were as follows: 1 cycle at 95° C. for 8 min, 42 cycles at 95° C. for 15 s, 60° C. for 1 min and 72° C. for 10 s. Target gene expression was normalized to the geometric mean of GAPDH and UBC housekeeping gene expression and relative quantification to the lowest expressing normal untreated control performed using the ΔΔCT method. Comparisons were made at 8 h post RV infection. IFN-β, RV-16, GAPDH and UBC detection was achieved using the following primers and fluorogenic probes:

```
IFN-β:
Probe:                                      (SEQ ID NO: 1)
FAM/TAMRA 5'TCAACATGACCAACAAGTGTCTCCTCCAA-3'

Forward primer                              (SEQ ID NO: 2)
5'-CACAACAGGTAGTAGGCGACAC-3'

Reverse primer                              (SEQ ID NO: 3)
5'-TGGAGAACAACAGGAGAG-3'

RV-16:
Probe:                                      (SEQ ID NO: 4)
FAM/TAMRA 5'CTTCGGATGGCAAGAGACACAGACCTGCt-3'

Forward primer                              (SEQ ID NO: 5)
5'-ACTGCTGAGATGTTGTGTTTTGTAT-3'

Reverse primer                              (SEQ ID NO: 6)
5'TGTTATTGGTCCTGTTTGCTTGTG-3'

UBC:
Probe:                                      (SEQ ID NO: 7)
VIC/TAMRA 5'-ACAGGGTGCGTCCATCTTCCAGC-3'

Forward primer                              (SEQ ID NO: 8)
5-GAGGTTGATCTTTGCTGGCAAAC-3

Reverse primer                              (SEQ ID NO: 9)
5-GGTGGACTCTTTCTGGATGTT-3

GAPDH:
Probe:                                      (SEQ ID NO: 10)
FAM/TAMRA 5'-CGTCGCCAGCCGAGCCACATCG-3'

Forward primer                              (SEQ ID NO: 11)
5-CAGAGTCAGCCGCATCTTCTT-3

Reverse primer                              (SEQ ID NO: 12)
5-TCCGTTGACTCCGAGCTTCA-3
```

IFN-β release in cell free culture supernatant was measured by ELISA (Biosource International) according to the manufacturer's instructions. The limit of sensitivity of the assay was >1.56 IU/ml for IFN-β.

Statistical Analysis

Data were analyzed using nonparametric equivalents and summarized using the median and interquartile range (IQR), multiple comparisons were first analyzed by the Kruskal Wallis test and then by individual testing if significant. For normally distributed data differences between groups were analyzed using Student's t test. A p-value of <0.05 was considered significant.

Results

Monolayer cultures of asthmatic cells were successfully infected with RV at an MOI of 2 to achieve cytopathic effects (CPE) (Wark et al. (2005) ibid), which were visible 8 hrs post-RV infection and accompanied by a 3 fold increase in LDH release 48 hrs post-RV infection. Therefore initial experiments were performed using monolayers of BECs from smokers without COPD and the same RV-16 stock at an MOI of 2. After 48 hrs, significant CPE>70% cytotoxicity was observed, as measured by LDH release into cell supernatants. This suggested that cells from smoking donors were more sensitive to RV-16 induced cytotoxicity than asthmatic cultures and that the extensive cell death in response to RV-16 infection in smokers may prevent secondary induction of anti-viral responses.

Dose and time course experiments were performed to follow RV-16 induction of cell lysis in monolayer cultures from smokers without COPD. Cultures were exposed to RV-16 at MOIs between 0.01-4, and RV induction of cytotoxicity was examined by LDH release at 8, 24 and 48 hrs. Robust cytopathic effects were observed 48 hrs post-viral infection at MOIs greater than 0.5. An MOI of 0.1 resulted in low cytotoxicity >20% at 24 hrs which increased to 40% cell lysis by 48 hrs post-RV infection. This dose was selected for use in further experiments.

Induction of IFNβ protein expression was measured by ELISA 48 hours after RV-16 infection, at a range of MOIs. A dose dependent trend towards decreased release of IFN-β with increasing virus dose was observed in smoker vs nonsmoker cultures. The significant increase in cell lysis in response to increasing MOI in smoker cultures most likely contributes to reduced numbers of viable cells and hence impaired release of IFN-β.

Comparison of RV-16 Infectious Viral Titre Released from BECs in Relation to Age and Smoking Status.

Primary BECs were infected with an MOI 2 and RV-16 release into the supernatant of infected cells 48 hrs post-RV infection was determined by calculating the $TCID_{50}$/ml ($\times 10^4$) by titration assay in Ohio HeLa cells. The supernatant from non-smoking young normals (n=10), non-smoking older normals (n=9), smokers without (n=7) and smokers with COPD (n=4) were examined on titration plates. By 48 hours there was a significant increase in release of infectious RV particles in the supernatant from smokers with and without COPD compared with healthy young non-smoker control cells (see FIG. 1; p<0.001 and p=0.007 respectively). Moreover, there was a trend towards more release of infectious RV particles with age comparing the results for the healthy young non-smokers (previously published in Wark et al. (2005) ibid) with the results for the healthy older non-smokers.

The cellular responses to RV-16 infection were compared in non-smokers and smokers using an MOI of 0.1. Viral replication was examined by determining levels of RV-16 vRNA expression 8 hours after infection. A significant increase in vRNA expression (3-fold) was observed in primary BECs from smokers compared with age matched non-smokers (p=0.014).

Figure 2A:
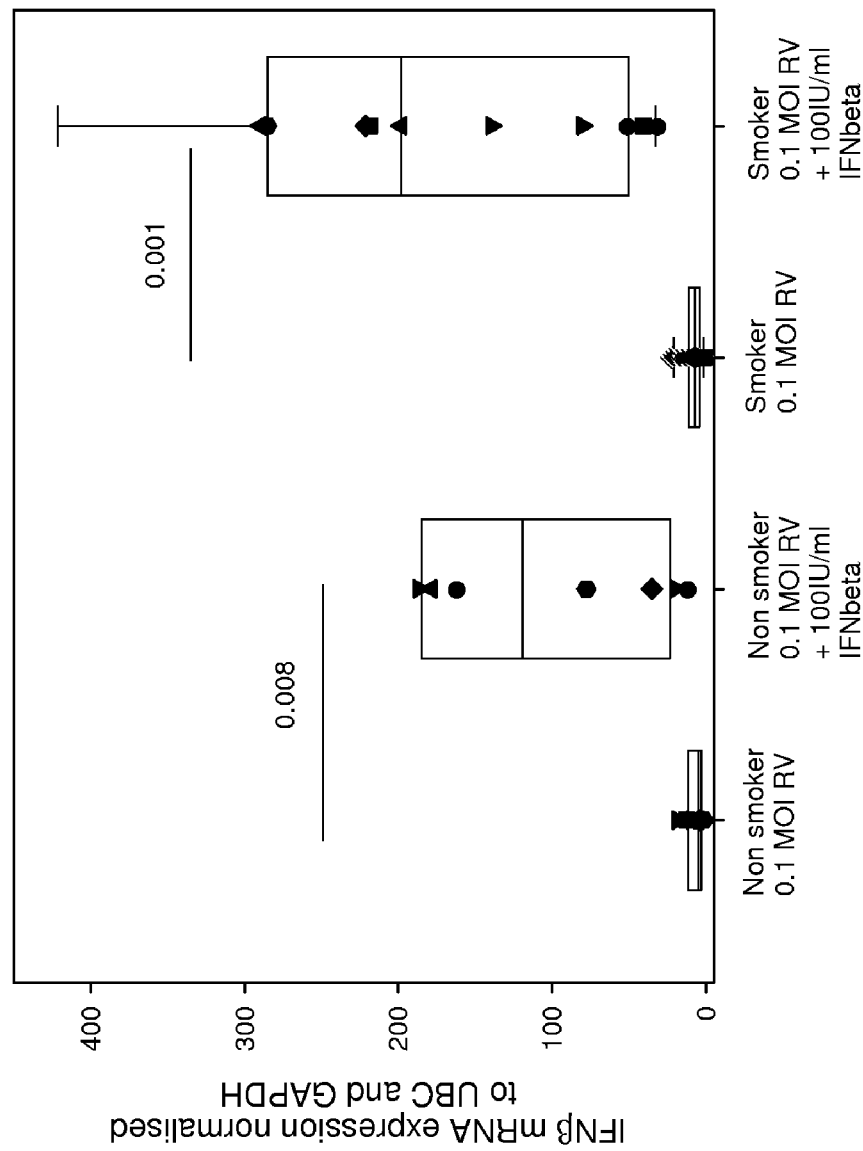
FIG. 2A: Induction of IFN-β gene expression was measured by qPCR after 8 hours of RV-16 infection and was normalised to the geometric mean of GAPDH and UBC housekeeping genes and relative quantitation was performed using the ΔΔCT method. RV-16 infection induced IFN-β expression was significantly up-regulated by pre-treatment by exogenous IFN-β (100 IU/ml) compared to RV treatment alone. IFN-β expression mean (IQR) increased from 5.3 (3.2, 11.5) to 119.4 (23.6, 184.6) in non-smokers (n=8; p=0.008) and from 7.2 (4.2, 11.1) to 198.1 (50.3, 285.1) in smokers (n=11; p<0.001).
Figure 2B:
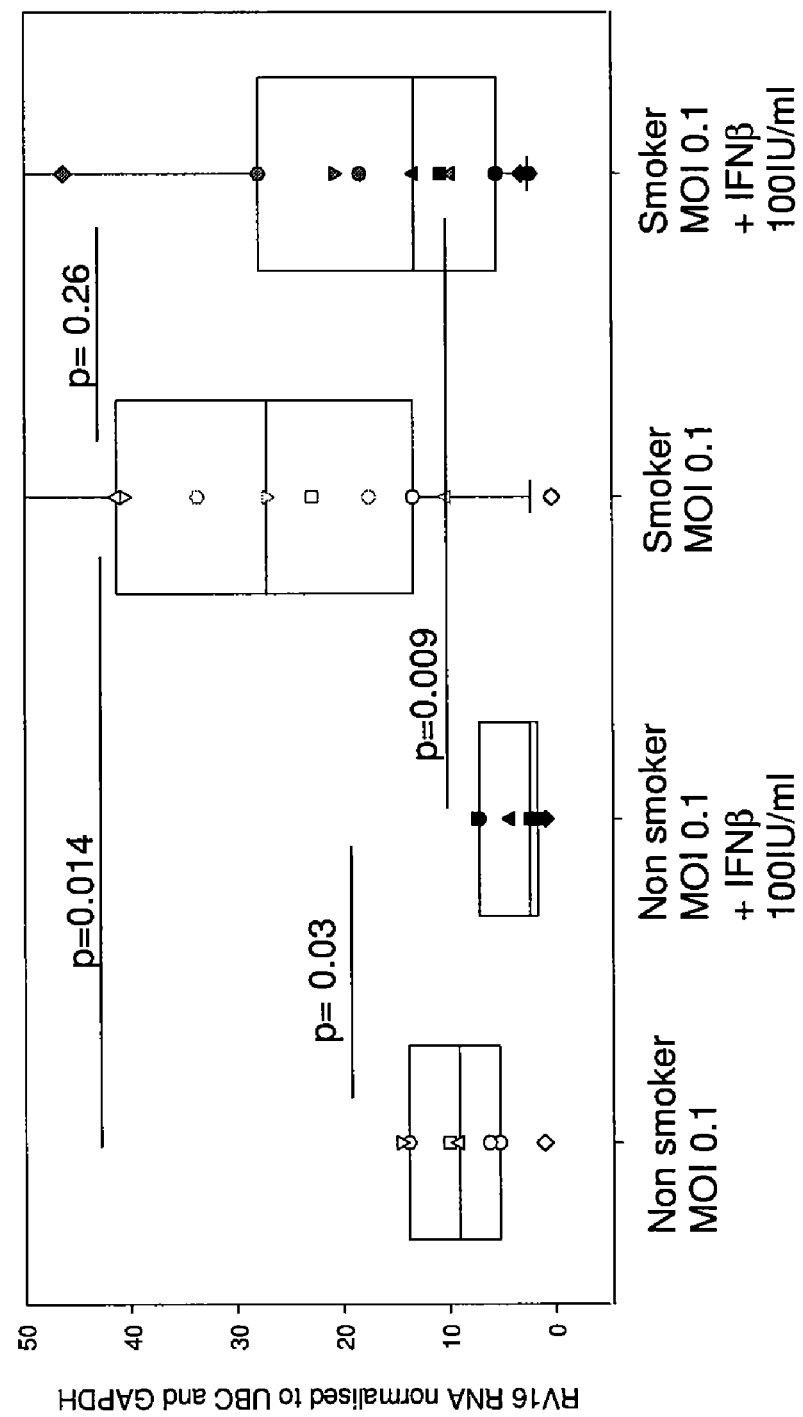
FIG. 2B: Addition of exogenous IFN-β induced a significant decrease in vRNA expression in non-smokers and a trend towards a decrease in smokers at 8 h (p=0.03).
Figure 2C:
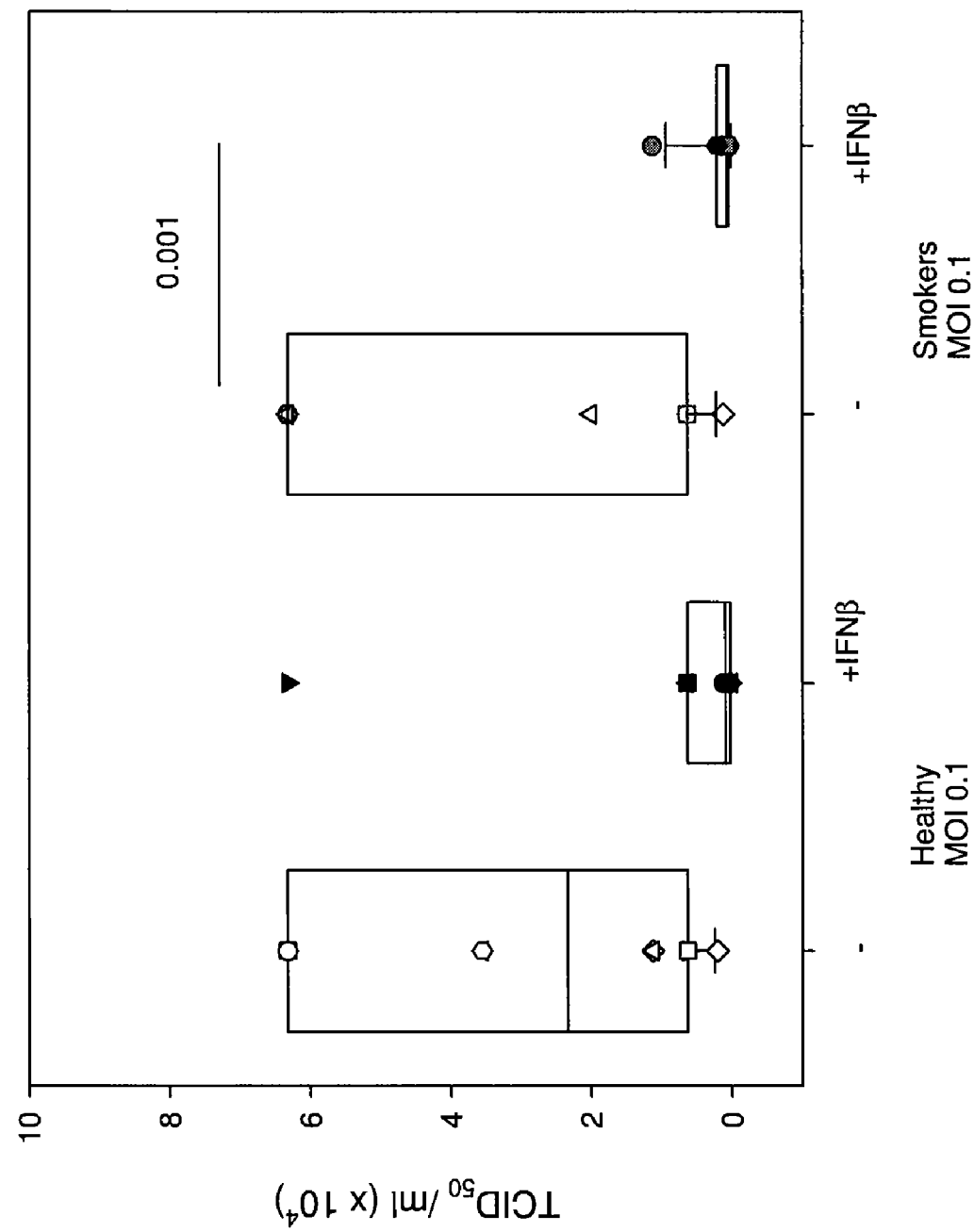
FIG. 2C: RV-16 release into the supernatant of infected cells was determined by calculating the $TCID_{50}$/ml ($\times 10^4$) by titration assay in Ohio HeLa cells. The supernatants from non-smokers (n=10) and smokers (n=11) were examined on titration plates. By 48 hours equivalent levels of infectious RV particles were detected in the supernatant from smokers and non-smokers. In the presence of IFN-β pre-treatment there were significant reductions in viral titres at 48 hrs post-infection from mean (SD) 6.32 (1.0) to 0.06 (0.05) in smokers compared to non-smokers (p<0.001). Data points represent the $TCID_{50}$/ml ($\times 10^4$). P<0.05 was considered significant.
Figure 2D:
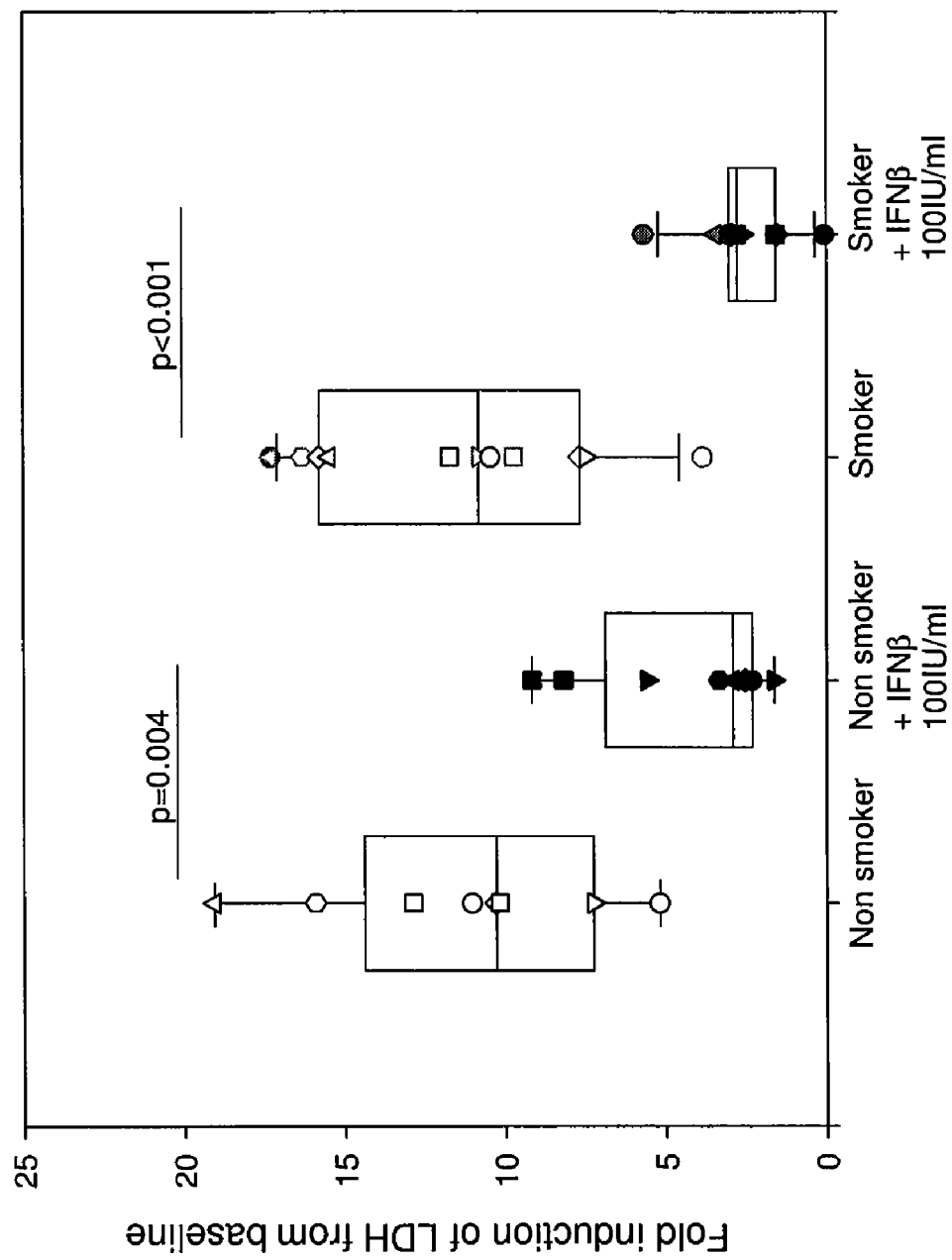
FIG. 2D: Induction of % total cell cytotoxicity in cultures was measured at 48 hrs by LDH release in to cell media and data presented as fold induction over control. Both non-smoker and smoker cultures treated with RV at an MOI 0.1 exhibited similar levels of cytotoxicity in response to RV infection. Exogenous IFN-β significantly reduced RV induced cell lysis in both groups from mean (SD) 11 (4.4) to 4.2 (2.8) in non-smokers and from 11.5 (4.3) to 2.64 (1.38) in smokers (p=0.004 and p<0.001 respectively).

LDH release into supernatants of both smoker and non-smoker cultures (p<0.001 and 0.004 respectively) (FIG. 2D).

Discussion

Primary BECs from age-matched smoker and non-smoker volunteers over the age of 40 are more susceptible to infection by RV-16 than primary BECs of young healthy non-smokers. Induction of cell death was dose and time dependent, higher viral MOIs led to more rapid induction of viral replication and cell lysis. CPE in cells from smokers was achieved at MOIs 0.01 to 0.1; in comparison similar CPE was observed in cultures from non-smoking young subjects at an MOI of 2. At 8 hrs there was increased virus replication in cells from smokers compared with those from non-smokers, although by 48 hrs there was no significant difference in viral titre. This may reflect a kinetic effect involving multiple rounds of viral replication approaching a common endpoint.

In RV-infected cells from smoking donors, exogenous IFN-β significantly reduced release of infective virus, reduced associated cell cytotoxicity and enhanced IFN-β expression.

The data for healthy older non-smokers provides an explanation for the previous data of Monto et al. referred to above and now set out below in Table 2 and suggests that airway delivery of IFN-β may also be worthwhile in such individuals, especially where poor clearance of RV-infection may lead to complication of other pre-existing or coincident medical conditions (El-Sahly et al ibid)

TABLE 1

Rhinovirus complications increase with age

| Age group (years) | No. of isolates | Illness with indicated syndrome (%) | | | | Median duration (days) | Percent with | |
|---|---|---|---|---|---|---|---|---|
| | | Lower respiratory | Upper respiratory | Laryngo-pharyngeal | Other | | Activity restriction | Physician consultation |
| 0-4 | 61 | 14.8 | 83.6 | 1.6 | — | 12 | 0 | 16.4 |
| 5-19 | 39 | 5.1 | 74.4 | 15.4 | 5.1 | 7 | 56.4 | 15.4 |
| 20-39 | 59 | 33.9 | 59.3 | 6.8 | — | 13 | 11.9 | 15.3 |
| ≧40 | 17 | 64.7 | 29.4 | 5.9 | — | 20 | 35.3 | 35.3 |
| Total | 176 | 23.8 | 68.2 | 6.8 | 1.2 | 12 | 19.9 | 17.6 |

Monto et al (1987) J. Infect. Dis. 156, 43

The Ability of Exogenous IFN-β to Modulate RV-16 Mediated Responses

We investigated whether reconstitution of Type 1 IFN responses in smoker cells with exogenous IFN-β was able to overcome the increased vRNA expression and trend towards increased RV replication observed in smoker primary BECs. IFN-β was added for 1 hr before RV infection and caused a significant increase in RV-induced IFN-β mRNA. This response was significantly augmented in the presence of exogenous IFN-β in healthy older non-smoker controls (23 fold; p=0.008) and smoker BECs (28 fold; p<0.001), 8 hours after RV-16 infection (FIG. 2A). The finding also suggests that induction of IFN-β expression is still functionally intact in cultures from smokers.

IFN-β caused a significant reduction in vRNA expression in cultures from non-smokers (p=0.03) with trend towards a decrease in cultures from smokers, 8 hrs post-RV exposure (FIG. 2B) Furthermore release of infectious RV-16 virus into supernatants was significantly attenuated by addition of IFN-β to cultures from smokers (p=0.001) (FIG. 2C). The protective effect of IFN-β was further highlighted by its ability to prevent virus induced cell cytotoxicity, measured by

REFERENCES

Carrat et al. (2006) "A virologic survey of patients admitted to a critical care unit for acute cardio-respiratory failure" Intensive Care Med. 32, 156-9.

Pistelli et al. (2003) "Determinants of prognosis of COPD in the elderly: mucus hypersecretion, infections, cardiovascular comorbidity". Eur. Respir. J. 21:10S-14S.

El-Sahly et al. (2000) "Spectrum of clinical illness in hospitalized patients with "common cold" virus infections." Clin Infect Dis. 31, 96-100.

Monto et al. (1987) "Rhinovirus infections in Tecumseh, Mich.: frequency of illness and number of Serotypes" J. Infect. Disease 156, 43.

Louie et al. (2005) "Rhinovirus outbreak in a long term care facility for elderly persons associated with unusually high mortality" Clinical Infect. Dis. 41, 262-265.

Falsey et al. (2002) "Rhinovirus and coronavirus infection-associated hospitalizations among older adults." J. Infect. Dis. 185, 1338-1341.

Cohen et al. (1993) "Smoking, alcohol consumption, and susceptibility to the common cold." Am. J. Public Health 83, 1277-1283.

Benseñor et al. (2001) "Active and passive smoking and risk of colds in women" AEP 11, 225-231;

Venarske et al. (2006) "The relationship of rhinovirus-associated asthma hospitalizations with inhaled corticosteroids and smoking." J. Infect Disease 193, 1536-1543

Wark et al. (2005) "Asthmatic bronchial epithelial cells have a deficient innate immune response to infection with rhinovirus" J. Exp. Med. 201, 937-947

Ank et al. (2006) "Lambda interferon (IFN-lambda), a type III IFN, is induced by viruses and IFNs and displays potent antiviral activity against select virus infections in vivo" J. Virol 80, 4501

Uzé et al. (2007) "IL-28 and IL-29: New comers to the IFN family" Biochimie epub ahead of print xx, 1-6

Contoli et al. (2006) "Role of deficient type III interferon-λ production in asthma exacerbations" Nat Med. 12, 1023-1026).

Higgins et al. (1986) "Interferon-beta ser as prophylaxis against experimental rhinovirus infection in volunteers" J. Interferon Res. 6, 153-159

Sperber et al. (1989) "Ineffectiveness of recombinant interferon-beta serine nasal drops for prophylaxis of natural colds" J. Infect. Dis. 160, 700-705

Chow et al. (1997) "Development of an epithelium-specific expression cassette with human DNA regulatory elements for transgene expression in lung airways." Proc. Nat. Acad. Sci. USA 94, 14695-14700.

Jones et al., (1992) "A self-complete measure of health status for chronic airflow limitation." Am. Rev. Respir. Dis. 145, 1321-1327.

Louis et al. (1999) "The effect of processing on inflammatory markers in induced sputum." Eur. Respir. J. 13, 660-667

Celli and MacNee (2004) "Standards for the diagnosis and treatment of patients with COPD: a summary of the ATS/ERS position paper." Eur. Respir J. 23, 932-946;

Fabbri and Hurd (2003) "Global Strategy for the Diagnosis, Management and Prevention of COPD: 2003 update" Eur. Respir. J. 22, 1-2

Hurd (2006) "Workshop summary and guidelines; investigative use of bronchoscopy" J. Allergy Clin. Immunol. 88, 808-814

Bucchieri et al. (2002) "Asthmatic bronchial epithelium is more susceptible to oxidant-induced apoptosis" Am. J. Respir. Cell. Mol. Biol. 27, 179-185;

Lordan et al. (2002) "Cooperative effects of Th2 cytokines and allergen on normal and asthmatic bronchial epithelial cells" J. Immunol. 169, 407-414

Papi and Johnson (1999) "Rhinovirus infection induces expression of its own receptor intercellular adhesion molecule 1 (ICAM-1) via increased NF-kappaB-mediated transcription." J. Biol Chem. 274, 9707-9720

The invention claimed is:

1. A method of treating rhinovirus (RV) infection in a non-asthmatic/non-COPD human individual of age 40 plus, which comprises airway delivery of an agent to the individual, wherein the agent is selected from the group consisting of
   (i) IFN-β and/or IFN-λ;
   (ii) agents that increase IFN-β and/or IFN-λ expression and
   (iii) polynucleotides which express one or more agents as in (i) or (ii) in human bronchial epithelial cells.

2. A method according to claim 1 wherein said individual is, or has been, a smoker, said individual being characterized by bronchial epithelial cells (BECs) which when infected in culture with RV exhibit increased cytotoxicity in response to RV infection compared with identically cultured BECS from non-smoker age-matched controls.

3. A method according to claim 1 wherein said individual has a clinical history of recurrent RV infection.

4. A method according to claim 2 wherein said individual has a clinical history of recurrent RV infection.

5. A method according to claim 1 wherein said individual is age 50 to 55.

6. A method according to claim 1 wherein said individual is age at least 60 to 65.

7. A method according to claim 1 wherein said individual is age at least 65 to 70.

* * * * *

```
                        SEQUENCE LISTING

<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: IFN beta probe

<400> SEQUENCE: 1
tcaacatgac caacaagtgt ctcctccaa                                     29

<210> SEQ ID NO 2
<211> LENGTH: 22
<212> TYPE: DNA
<213> ORGANISM: Artificial Sequence
<220> FEATURE:
<223> OTHER INFORMATION: Forward primer

<400> SEQUENCE: 2
cacaacaggt agtaggcgac ac                                            22

<210> SEQ ID NO 3
<211> LENGTH: 18
<212> TYPE: DNA
<213> ORGANISM: Artificial Sequence
<220> FEATURE:
<223> OTHER INFORMATION: Reverse primer

<400> SEQUENCE: 3
tggagaacaa caggagag                                                 18

<210> SEQ ID NO 4
<211> LENGTH: 29
```

```
<212> TYPE: DNA
<213> ORGANISM: Artificial Sequence
<220> FEATURE:
<223> OTHER INFORMATION: RV-16 probe

<400> SEQUENCE: 4
cttcggatgg caagagacac agacctgct                              29

<210> SEQ ID NO 5
<211> LENGTH: 25
<212> TYPE: DNA
<213> ORGANISM: Artificial Sequence
<220> FEATURE:
<223> OTHER INFORMATION: Forward primer

<400> SEQUENCE: 5
actgctgaga tgttgtgttt tgtat                                  25

<210> SEQ ID NO 6
<211> LENGTH: 24
<212> TYPE: DNA
<213> ORGANISM: Artificial Sequence
<220> FEATURE:
<223> OTHER INFORMATION: Reverse primer

<400> SEQUENCE: 6
tgttattggt cctgtttgct tgtg                                   24

<210> SEQ ID NO 7
<211> LENGTH: 23
<212> TYPE: DNA
<213> ORGANISM: Artificial Sequence
<220> FEATURE:
<223> OTHER INFORMATION: UBC probe

<400> SEQUENCE: 7
acagggtgcg tccatcttcc agc                                    23

<210> SEQ ID NO 8
<211> LENGTH: 23
<212> TYPE: DNA
<213> ORGANISM: Artificial Sequence
<220> FEATURE:
<223> OTHER INFORMATION: Forward primer

<400> SEQUENCE: 8
gaggttgatc tttgctggca aac                                    23

<210> SEQ ID NO 9
<211> LENGTH: 21
<212> TYPE: DNA
<213> ORGANISM: Artificial Sequence
<220> FEATURE:
<223> OTHER INFORMATION: Reverse primer

<400> SEQUENCE: 9
ggtggactct ttctggatgt t                                      21

<210> SEQ ID NO 10
<211> LENGTH: 22
<212> TYPE: DNA
<213> ORGANISM: Artificial Sequence
<220> FEATURE:
<223> OTHER INFORMATION: GAPDH probe

<400> SEQUENCE: 10
```

-continued

```
cgtcgccagc cgagccacat cg                                          22

<210> SEQ ID NO 11
<211> LENGTH: 21
<212> TYPE: DNA
<213> ORGANISM: Artificial Sequence
<220> FEATURE:
<223> OTHER INFORMATION: Forward primer

<400> SEQUENCE: 11
cagagtcagc cgcatcttct t                                           21

<210> SEQ ID NO 12
<211> LENGTH: 20
<212> TYPE: DNA
<213> ORGANISM: Artificial Sequence
<220> FEATURE:
<223> OTHER INFORMATION: Reverse primer

<400> SEQUENCE: 12
tccgttgact ccgagcttca                                             20
```